United States Patent
Perricone

(10) Patent No.: US 8,273,711 B2
(45) Date of Patent: *Sep. 25, 2012

(54) TOPICAL DRUG DELIVERY USING PHOSPHATIDYLCHOLINE

(75) Inventor: Nicholas V. Perricone, Meriden, CT (US)

(73) Assignee: Transdermal Biotechnology, Inc., Meriden, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/024,689

(22) Filed: Feb. 10, 2011

(65) Prior Publication Data

US 2011/0130330 A1   Jun. 2, 2011

Related U.S. Application Data

(60) Continuation of application No. 11/334,206, filed on Jan. 18, 2006, now abandoned, which is a division of application No. 10/448,632, filed on May 30, 2003, which is a continuation of application No. 11/344,442, filed on Jan. 31, 2006, now abandoned, which is a division of application No. 10/749,914, filed on Dec. 31, 2003, now Pat. No. 7,182,956.

(60) Provisional application No. 60/384,597, filed on May 31, 2002, provisional application No. 60/437,279, filed on Dec. 31, 2002.

(51) Int. Cl.
| | |
|---|---|
| *A61K 38/28* | (2006.01) |
| *A61K 38/31* | (2006.01) |
| *A61K 38/36* | (2006.01) |
| *A61K 38/00* | (2006.01) |
| *A61K 38/27* | (2006.01) |
| *A61K 38/23* | (2006.01) |
| *A61K 38/24* | (2006.01) |
| *A61K 38/11* | (2006.01) |
| *A61K 47/00* | (2006.01) |
| *A61K 31/685* | (2006.01) |
| *A01N 57/26* | (2006.01) |

(52) U.S. Cl. ........... 514/5.9; 514/78; 514/806; 514/807; 514/808; 514/866; 514/970

(58) Field of Classification Search ..................... None
See application file for complete search history.

(56) References Cited

U.S. PATENT DOCUMENTS

| | | | | |
|---|---|---|---|---|
| 5,955,502 | A | * | 9/1999 | Hansen et al. ............... 514/558 |
| 5,985,298 | A | * | 11/1999 | Brieva et al. ................ 424/401 |
| 6,022,561 | A | * | 2/2000 | Carlsson et al. ............. 424/450 |
| 6,538,061 | B2 | * | 3/2003 | Chaiyawat et al. .......... 524/806 |

OTHER PUBLICATIONS

Prescott, Methods in Cell Biology, Academic Press 1976 chapter 4, p. 34: 4 pages.*

* cited by examiner

*Primary Examiner* — Ernst Arnold

(74) *Attorney, Agent, or Firm* — St. Onge Steward Johnston & Reens LLC

(57) ABSTRACT

The present invention relates to compositions and methods for transdermal drug delivery comprising formulating a phosphatidylcholine carrier composition containing the drug and applying the composition to the skin.

10 Claims, No Drawings

TOPICAL DRUG DELIVERY USING PHOSPHATIDYLCHOLINE

CROSS REFERENCE TO RELATED APPLICATIONS

This application is a continuation of pending U.S. patent application Ser. No. 11/334,206 for "Topical Drug Delivery Using Phasphatidylcholine" filed Jan. 18, 2006, which is a divisional of pending U.S. patent application Ser. No. 10/448,632 for "Topical Drug Delivery Using Phosphatidylcholine" filed May 30, 2003, which claims priority benefits under 35 U.S.C. §119(e) of U.S. Provisional Patent Application No. 60/384,597 filed May 31, 2002. This application is also a continuation of pending U.S. patent application Ser. No. 11/344,442 filed Jan. 31, 2006, which is a divisional of U.S. patent application Ser. No. 10/749,914 filed Dec. 31, 2003, now U.S. Pat. No. 7,182,956 issued Feb. 27, 2007, which claims priority benefits under 35 U.S.C. §119(e) of U.S. Provisional Patent Application No. 60/437,279 filed Dec. 31, 2002.

FIELD OF THE INVENTION

The present invention relates to a topical drug delivery composition and method. More specifically, this invention relates to topical drug delivery compositions and methods using phosphatidylcholine.

BACKGROUND OF THE INVENTION

Transdermal drug delivery systems may be designed to act locally at the point of application or to act systemically by entering the body's blood circulation. In these systems, delivery may be achieved by direct topical application of a substance or drug in the form of an ointment or the like, or by adhesion of a patch with a reservoir that holds the drug and releases it to the skin in a time-controlled fashion.

Transdermal delivery systems for agents such as drugs, pain relieving compounds, vitamins, and skin improving compounds have been in use for a number of years. However, these systems have typically only been useful for transdermal delivery of relatively small molecules. The skin's porous structure permits such small molecules to pass from the epidermis to the dermis via diffusion. These transdermal delivery systems such as creams have been developed for use with analgesics and skin refining compounds. Transdermal systems using a patch have been developed for nicotine and estrogen therapies. Estradiol technologies are described in U.S. Pat. No. 6,521,250 to Meconi, et al. However, large molecules, such as insulin, are not able to diffuse through the skin. To date there has not been an effective and economical method to transport such molecules through the epidermis to enter the bloodstream via the dermal vasculature.

It has been proposed that molecules, potentially including larger molecules, can be transported through the skin when such molecules are contained within spherical vesicles, variously called microparticles, microspheres, liposomes, lipid vesicles, transfersomes, formed by hydrating a phospholipid. The resulting vessels are water-insoluble and are dispersed and suspended in a liquid base material which is applied to the skin to deliver the drug. U.S. Pat. No. 6,165,500 to Cevc discloses "transfersomes," which are vesicles containing both a lipid and surfactant, to achieve transdermal delivery, based on a theory that osmotic pressure will drive the transfersomes through the dermis. Other solutions have been proposed, including the use of ultrasound devices to generating shock waves to enlarge pores, use of electric current to drive substances across skin, and the use of microneedles to pierce skin and deliver drugs into bloodstream. (See *More Than the Patch: New Ways to Take Medicine Via Skin*, New York Times, Jul. 2, 2002, page F5.)

There remains a need for a transdermal drug delivery system with the improved skin permeability and ability to transport a wider range of substances or drugs. This problem is particularly apparent in the transdermal delivery of substances composed of large molecules, such as polypeptides or proteins, which do not readily pass through the pores of the skin. Absent such a transdermal drug delivery system, the use of injections to deliver these substances will remain the conventional dosage method, despite the pain, complicated administration and general invasiveness involved therein.

SUMMARY OF THE INVENTION

The present invention relates to compositions and methods of transdermal drug delivery comprising formulating a composition containing the drug in a crystallized phosphatidylcholine carrier and applying the composition to the skin.

DETAILED DESCRIPTION OF THE INVENTION

The disclosure of U.S. patent application Ser. No. 11/344,442 filed Jan. 31, 2006, for "Methods of Delivering Topical Drug Compositions," is hereby incorporated by reference.

Phosphatidylcholine is used as a carrier for the topical drug delivery of macromolecules in the practice of this invention. Phosphatidylcholine is a basic component of cell membrane bilayers and the main phospholipid circulating in the plasma. Phosphatidylcholine is highly absorbable and supplies choline which is needed to facilitate movement of fats and oils across and maintain cell membranes in animals.

Phosphatidylcholine compositions (herein abbreviated "PC compositions") of the present invention are formulated to contain macromolecules soluble in PC, which are then applied to skin for transdermal delivery of the macromolecule. PC compositions of the invention are efficacious in the delivery of macromolecular drugs that are conventionally administered intramuscularly, intravenously or orally, including, but not limited to polypeptides such as insulin and somatropin, prostaglandins, glucocorticoids, estrogens, androgens, and the like.

It is an advantage of the invention that topical delivery is easier and pleasanter as an administration route than injections, particularly for drugs such as insulin that must be given to patients over a period of time, or for a lifetime. Furthermore, unlike oral administration where a substantial amount of the drug can be destroyed in the digestive process, the drugs in a topical application are not wasted. Topical application allows a steady diffusion of the drug to the desired target area without the cyclic dosages typical of orally or parenterally administered drugs.

Typical phosphatidylcholine compositions of the present invention are nonpolar and contain about 85% phosphatidylcholine. By "phosphatidylcholine" is meant a mixture of stearic, palmitic, and oleic acid diglycerides linked to the choline ester of phosphoric acid, commonly called lecithin. Many commercial lecithin products are available, such as, for example, Lecithol®, Vitellin®, Kelecin®, and Granulestin® because lecithin is widely used in the food industry. Compositions of the invention can contain synthetic or natural lecithin, or mixtures thereof. Natural preparations are preferred because they exhibit desirable physical characteristics and are both economical and nontoxic.

The macromolecular drugs are mixed with the PC composition under conditions to become entrapped in a phosphatidylcholine bilayer. Phosphatidylcholine forms a bilayer entrapping the macromolecular drug, which may be a polypeptide, contributing to the stability of the active molecule and enhancing penetration. The PC composition therein comprises a carrier-drug combination to be applied topically.

While not wishing to be bound by any particular theory, it is believed that the following mechanism illustrates how the PC composition acts to efficiently transport the drug across the epidermis, maximizing penetration of the drug. The PC composition, in liquid crystal phase, is loosely arranged in multilamellar fashion, with the drug being bonded and entrapped within the lipid bilayers formed by the PC composition. This forms a loosely arranged, yet stable, PC composition carrier-drug complex. When placed on the epidermis, the carrier-drug complex begins to diffuse through the epidermis. The phosphatidylcholine molecular chain remains loosely linked with the drug molecular chain and the diffusing phosphatidylcholine molecules "drag" the drug molecules along as they pass through the skin layers. Moreover, the phosphatidylcholine molecules may begin to separate from the loosely arranged carrier-drug complex and become integrated into the dermis. As the phosphatidylcholine molecules separate from the crystallized phophoslipid bilayer structure of the carrier-drug complex the drug molecules are released. As these drug molecules are released, they are now within into the dermis and may enter the dermal vasculature so they may act accordingly in the bloodstream. Drug molecules which were once too large to diffuse, by themselves, into the pores of the epidermis, have instead been forced through the epidermis by phosphatidylcholine carriers which naturally enter and integrate into lipid bilayer structures within the cells of the epidermis and/or dermis and resultantly are required to release their bonds to the drug molecules and set them free within the dermis.

Preferred PC compositions comprise phosphatidylcholine in crystal phase to increase fluidity of the lipid bilayer formed. By reducing rigidity and loosening the phospholipid bilayer of the PC composition, larger molecules may embed therein and penetration of the carrier-drug composition by the cell membrane is facilitated. The skin is more permeable to the fluid, less structured lipid bilayer of the PC/carrier-drug composition applied thereon than to the drug by itself, or entrapped in an organized, arranged vesicle such as a liposome. The loosely packed lipid bilayer of the crystallized carrier-drug composition integrates into the cell membrane, and as a result, has transported the drug so it can enter the bloodstream to act upon the body. The PC composition may be a multilamellar liquid crystal phase or a liquid crystal phase suspension in water which may be converted to multilamellar liquid lipid vesicles.

In preferred embodiments, nonpolar preparations of phosphatidylcholine are formulated to contain adjunct ingredients, e.g., lipoic acid and ascorbyl palmitate, in addition to the macromolecular drug. The adjunct ingredients act synergistically to help to minimize degradation and thus preserve the integrity of the insulin polypeptide chains, and to enhance transdermal penetration of active insulin so that it can be absorbed by the dermal vasculature.

Preferred PC compositions of the invention contain some polyenylphosphatidylcholine (herein abbreviated "PPC") to enhance epidermal penetration. By "polyenylphosphatidylcholine" is meant any phosphatidylcholine bearing two fatty acid substituents, wherein at least one is an unsaturated fatty acid with at least two double bonds such as linoleic acid. Preferred PPCs contain a mixture of substitutents such as those found in natural products such as soybean lecithin, which contains 11.7% palmitic, 4.0% stearic, 8.6% palmitoleic, 9.8% oleic, 55.0% linoleic, and 4.0% linolenic acid substituents and is a by-product of soybean oil manufacture.

Certain types of soybean lecithin, for example, contain higher levels of polyenylphosphatidylcholine, with dilinoleoylphosphatidylcholine (18:2-18:2 phosphatidylcholine) as the most abundant phosphatidylcholine species, than conventional food grade lecithin, and are useful in formulating phosphatidylcholine insulin compositions of the invention. Alternatively, conventional soybean lecithin is enriched with PPC by adding soybean extracts containing high levels of PPC. As used herein, this type of phosphatidylcholine is called "PPC-enriched" phosphatidylcholine, even where the term encompasses lecithin obtained from natural sources exhibiting PPC levels higher than ordinary soybean varieties. These products are commercially available from American Lecithin, Rhône-Poulenc and other lecithin vendors. American Lecithin markets its products with a "U" designation, indicating high levels of unsaturation; Rhône-Poulenc's product is a soybean extract containing about 42% dilinoleoylphosphatidylcholine and about 24% palmitoyllinoleylphosphatidylcholine (16:0-18:2 PC) as the major PC components.

PC compositions are used for transdermal polypeptide delivery in some preferred embodiments. Polypeptide drugs that are delivered transdermally using formulations can be small, e.g., ocytocin and vasopressin nonapeptides or large, e.g., insulin, gonadotropin, and somatropin. PC compositions of the invention deliver drugs including, but are not limited to, oxytocin, vasopressin, insulin, somatotropin, calcitonin, chorionic gonadotropin, menotropins, follitropins, somatostatins, progestins, and combinations of any of these. These drugs are readily available from a variety of commercial sources. Insulin, for example, is marketed under the tradenames Humulin®, Novolin®, Humalog®, and Inutral®. Somatotropin is marketed under the tradenames Gentropin®, Humatrope®, Nutropin®, and Serostim®. Some of these products and other polypeptides contain porcine sequences. Preferable compositions of the invention are preferably formulated with recombinant human polypeptides. It is an advantage of the invention that PC insulin compositions are formulated with commercially available ingredients.

One, non-limiting, example of an insulin topical preparation was formulated by combining 0.75% methyl paraben with a commercial phosphatidylcholine preparation marketed as a solution denoted NAT-8729 (containing PEG-400 at 40% and P.G. at 5%) by mixing for an hour or more to emulsify. To this is slowly added Dow Corning Fluid 200-5 or 10 cst (1% by weight), the formulation is mixed, and then Dow Corning Fluid 190 (1% by weight) is slowly added, and the formulation is further mixed to provide a stock insulin carrier. Prior to topical administration, insulin is added at a level of about 3.8 mg/ml to provide about 100 insulin units per ml.

Another, non-limiting, example of a pituitary growth hormone (somatotropin) composition was formulated with 85% phosphatidylcholine to which lipoic acid and ascorbyl palmitate was added as antioxidants. Somatotropin readily dispersed in phosphatidylcholine and remained stable in it. Growth hormone appeared to penetrate the skin well when the composition was topically applied.

It is appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modification be covered by the following claims.

What is claimed is:

1. A stable transdermal insulin composition comprising a phosphatidylcholine component, said phosphatidylcholine component comprising polyenylphosphatidylcholine-enriched phosphatidylcholine and at least one polyglycol, and forming a non-liposomal multilamellar liquid crystal carrier entrapping said insulin for transdermal delivery to dermal vasculature, wherein said multilamellar liquid crystal carrier stabilizes the insulin at room temperature, wherein said phosphatidylcholine component comprises 45% w/w phosphatidylcholine, 50% w/w polyglycol having a molecular weight of 200 and 5% w/w polyglycol having a molecular weight of 400.

2. The transdermal composition of claim 1, further comprising a surfactant, and a lubricant, and methyl paraben.

3. The transdermal composition of claim 2, wherein
said surfactant is a siloxylated polyether; and
said lubricant is silicone fluid.

4. The transdermal composition of claim 3, wherein
said siloxylated polyether is dimethyl, methyl(propylpolyethylene oxide propylene oxide, acetate) siloxane; and
said silicone fluid contains low viscosity polydimethylsiloxane polymers.

5. A stable transdermal therapeutic composition comprising a phosphatidylcholine component, said phosphatidylcholine component comprising polyenylphosphatidylcholine-enriched phosphatidylcholine and at least one polyglycol, and forming a non-liposomal multilamellar liquid crystal carrier entrapping a therapeutic compound for transdermal delivery to dermal vasculature, wherein said multilamellar liquid crystal carrier stabilizes the therapeutic compound at room temperature, wherein said phosphatidylcholine component comprises 45% w/w phosphatidylcholine, 50% w/w polyglycol having a molecular weight of 200 and 5% w/w polyglycol having a molecular weight of 400.

6. The transdermal composition of claim 5, further comprising a surfactant, and a lubricant, and methyl paraben.

7. The transdermal composition of claim 6, wherein
said surfactant is a siloxylated polyether; and
said lubricant is silicone fluid.

8. The composition of claim 5, wherein the therapeutic compound is selected from the group consisting of oxytocin, vasopressin, insulin, somatotropin, calcitonin, chorionic gonadotropin, menotropins, follitropins, somatostatins, progestins, and combinations of any of these.

9. The composition of claim 5, wherein the phosphatidylcholine is pure polyenylphosphatidylcholine.

10. The composition of claim 5, wherein the composition contains about 85% phosphatidylcholine.

* * * * *